United States Patent [19]

Grass et al.

[11] 4,288,700
[45] Sep. 8, 1981

[54] CABLE HANDLING DEVICE FOR DIAGNOSTIC X-RAY APPARATUS

[75] Inventors: Joseph J. Grass; David M. Barrett, both of Brookfield; Randolph N. Wendt, Milwaukee, all of Wis.

[73] Assignee: General Electric Company, Schenectady, N.Y.

[21] Appl. No.: 86,881

[22] Filed: Oct. 22, 1979

[51] Int. Cl.³ .................. H01J 35/16; H02G 15/08
[52] U.S. Cl. .................................. 250/523; 250/402; 174/86
[58] Field of Search ............ 250/523, 491, 445 T, 250/402; 285/61, 64, 272, 273, 274; 248/49, 48; 174/86; 191/12 R

[56] References Cited
U.S. PATENT DOCUMENTS 3,381,711  5/1968  Fye et al. .................. 248/58
4,002,357  1/1977  Bennett ...................... 285/114

Primary Examiner—Alfred E. Smith
Assistant Examiner—Carolyn E. Fields
Attorney, Agent, or Firm—Wheeler, House, Fuller & Hohenfeldt

[57] ABSTRACT

A device for handling a group of cables running to medical x-ray equipment that is movable in all degrees of freedom comprises: A vertical axle mounted overhead; a boom swingable in a horizontal plane on the axle; a housing on the axle having openings for receiving and clamping the ends of respective flexible cable enclosing tubes, one of which extends over the boom to the equipment and the other of which establishes a cable path continuing to a swivel mechanism that is spaced from the axle and mounted overhead.

6 Claims, 5 Drawing Figures

CABLE HANDLING DEVICE FOR DIAGNOSTIC X-RAY APPARATUS

The invention described herein is an improved device for handling a group of electric cables which lead to and from medical x-ray equipment. The new device is particularly useful for handling cables affiliated with x-ray equipment that is specially designed for making vascular examinations, particularly, cardiovascular examinations.

A type of vascular examination equipment, which came into use recently enough to be called new, created unusual cable handling problems that could not be solved satisfactorily by utilizing prior art pertaining to cable handling devices. The x-ray equipment under consideration comprises an L-shaped arm hereafter called an L-arm having horizontal and vertical portions. The horizontal portion has its end floor-mounted for rotation about a vertical axis in a horizontal plane that is parallel to the floor of the room in which the equipment is located. The L-arm can be swung through substantially 360° over a large circular area above the floor. A U-shaped arm (hereafter called a U-arm) comprised of a radially extending base section and two additional sections which extend axially from opposite ends of the radially extending base section is mounted for rotation about a horizontal axis at the upper end of the upstanding section of the L-arm.

An x-ray tube and collimator assembly is mounted at the end of one of the axially extending sections of the U-arm and an x-ray image intensifier is mounted in alignment with the x-ray source on the other axially extending section of the U-arm. The U-arm and L-arm mounting combination permits moving the x-ray source and image intensifier through substantially all required angles to enable obtaining x-ray views of a patient disposed between the source and intensifier from any perspective.

About a dozen electrical cables are usually necessarily connected to this equipment. For instance, there are some stiff, well-insulated cables for supplying high voltage between the cathode and anode of the x-ray tube. There are cables for energizing the stator of the rotating anode x-ray tube rotor and there are conductors for supplying the filament of the tube. Additional cables are required for the x-ray image intensifier and for the cine camera and video camera which are usually mounted to the intensifier. Further cables are required for motors that adjust the distance between the focal spot of the x-ray tube and the image plane of the intensifier. Other cables are required for the motors that adjust the collimator blade openings.

It is important that the components of the equipment be counterpoised so that the x-ray source and image intensifier assembly will have a tendency to remain where the radiologist positions them by swinging the L-arm and turning the U-arm. It is undesirable to let stress build up in the cable bundle since internal stress would tend to change the position of the equipment components and require additional effort on the part of the radiologist to overcome. It is also important that the cables not interfere with movements of the equipment components nor with the movements of the radiologist in the work area nor with movements of other x-ray equipment which is almost always present in vascular examination rooms. Additional requirements are that: A wide range of L and U arm positions should be obtainable; cable protection and esthetic quality should be maximized; use in a room with relatively low ceilings should be permissible; and, the device should be compatible with bi-plane and single-plane x-ray systems as well.

SUMMARY OF THE INVENTION

An object of the invention is to provide a cable handling device that fulfills the above-mentioned and other requirements which will be more fully discussed hereinafter.

In accordance with the invention, a horizontally extending cable supporting boom is mounted for rotating about a vertical axis in a horizontal plane above the x-ray equipment. The cables extend from the x-ray equipment to the boom on which the cables are supported. The cables continue from the boom to a swivel mechanism which turns on a vertical axis that is parallel to the boom axis and spaced from it. The swivel mechanism provides a path for the cables from the boom to the various stationary electrical devices in the room to which the cables are connected and relieves torsional stress from the cables. Flexible tubes extend from the boom to the swivel mechanism and from the boom to the x-ray equipment to protect and conceal the cables. The cables run loosely through the tubes and additional stiffness which would otherwise be imparted to them by bundling them is avoided.

A more detailed description of a preferred embodiment of the new cable handling device will now be set forth in reference to the drawings.

DESCRIPTION OF A PREFERRED EMBODIMENT

Figure 1:
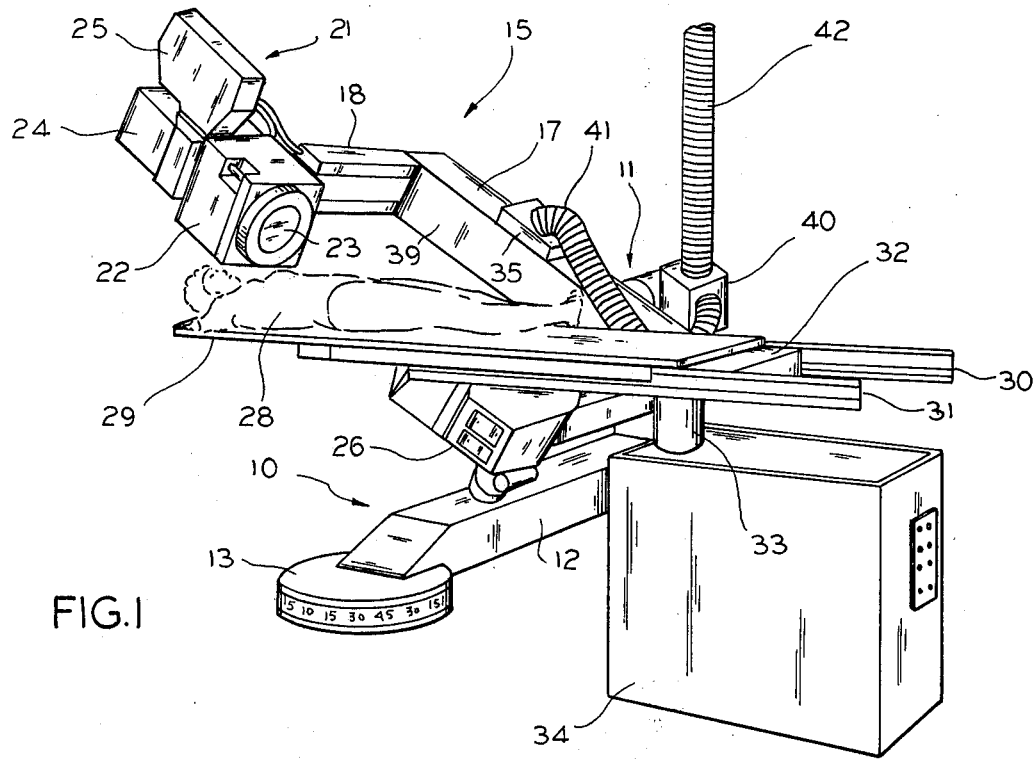
FIG. 1 is a perspective view of vascular examination x-ray equipment with which the new cable handling device may be used.

Before describing the new cable handling device in detail, the general features of typical x-ray equipment with which the device may be used will be described in reference to FIGS. 1 and 2. The L-arm is designated generally by the reference numeral 10. It is comprised of an upstanding arm section 11 and a horizontally extending section 12. One end of section 12 terminates in a circular housing 13 which encloses a floor mounted bearing, not visible, that supports horizontally extending L-arm section 12 for swinging about a vertical axis in a horizontal plane that is parallel to the floor 14 of the x-ray procedure room.

A U-arm, generally designated by the numeral 15, is supported on a pintle 16 for rotation about a horizontal axis in parallelism with upstanding L-arm section 11. U-arm 15 is composed of a base section 17 which extends radially to opposite sides of pintle axis 16. The U-arm further comprises axially extending sections 18 and 19. A guide 20 is supported for translating at the outstanding end of U-arm section 18 and an x-ray image intensifier assembly 21 is mounted on the guide for being translated with it. X-ray image intensifier assembly 21 includes an image tube housing 22 having a window 23 for entry of the x-ray beam and the image which it entrains into the x-ray image intensifier which occupies the housing. Associated with image intensifier assembly 21 is a video camera and a cine camera symbolized by the items marked 24 and 25.

The outboard end of axially extending section 19 of U-arm 15 supports an x-ray tube housing 26 which has motor operated x-ray beam collimator 27 coupled with it. An x-ray source in housing 26 projects an x-ray beam toward the image intensifier input window 23 and through a patient intervening between the source and intensifier. A typical patient or x-ray examination subject is marked 28 and is shown in FIG. 1 as being supported on an x-ray transmissive table top 29 which is mounted for translating on tracks 30 and 31. The tracks are mounted to a support 32 which is further supported on a column 33 extending from a floor mounted enclosure 34. It will be evident that by swinging L-arm 10 circularly in a horizontal plane about the vertical axis going through the floor mounted bearing housing 13 and turning the U-arm on the axis of pintle 16, the x-ray beam may be projected into perpendicularity with any desired plane in the patient's body as is necessary to obtain adequate diagnostic information from vascular examinations.

Figure 2:
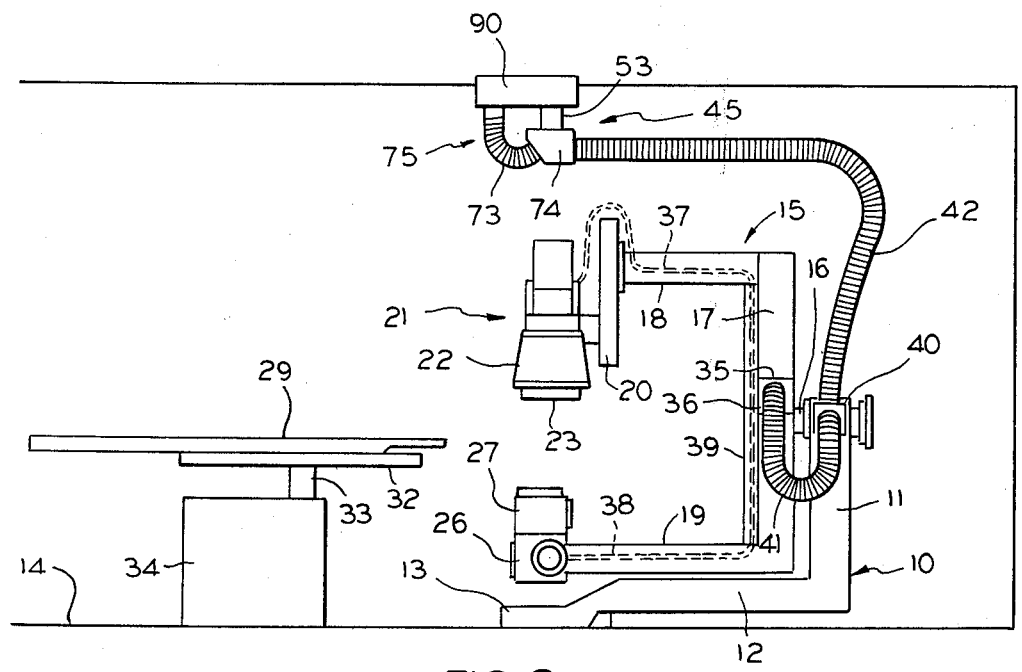
FIG. 2 provides a side elevational view of the vascular examination equipment and a general view of the cable handling device.
Figure 5:
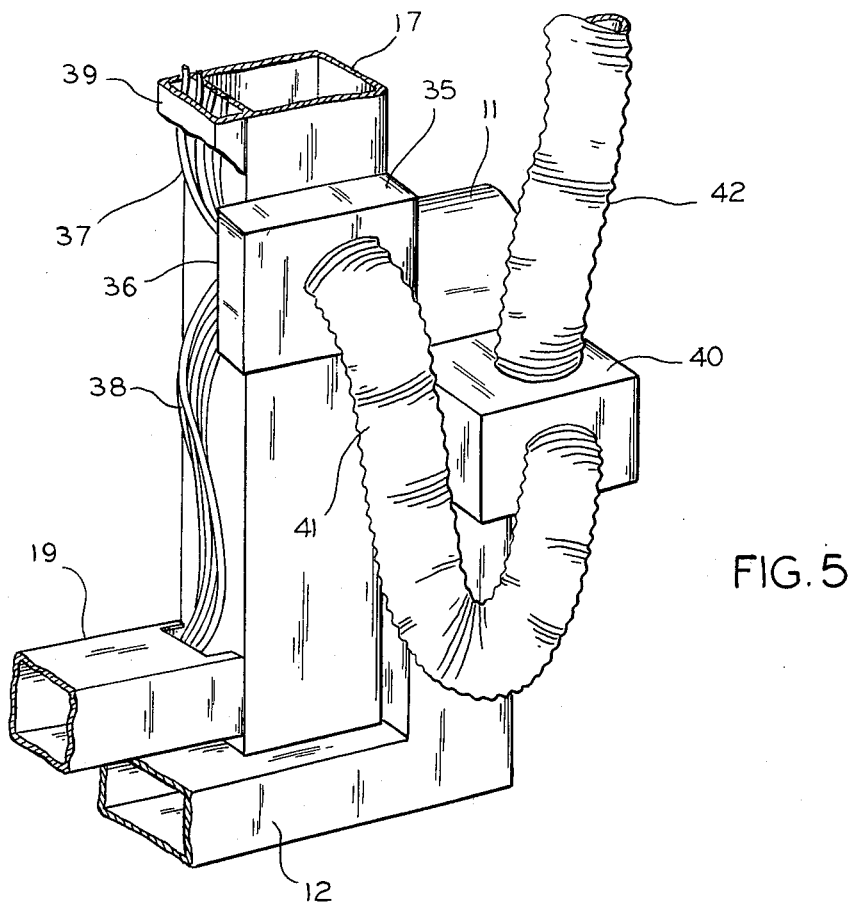

Referring to FIG. 2, there is a junction box 35 mounted on the side of U-arm section 17 which is nearest to the observer in this figure and which is also on the side of the observer in FIG. 5. This junction box has an opening 36 in its backside which extends frontwardly beyond the inside plane of arm section 17 to permit passage of cables through box 35. The multiplicity of cables leading from the image intensifier assembly 21 are represented by a dashed line 37 and the cables leading from the x-ray tube and collimator assembly 26, 27 are represented by the dashed line 38. A cover for these cables, running along the side of U-arm base section 17, is symbolized by the solid line 39. Another box 40 is mounted on the front side of upstanding section 11 of L-arm 10 as shown in FIGS. 1, 2 and 5.

FIG. 5 provides a direct view of box 35 mounted on section 17 of the U-arm and box 40, mounted on section 11 of the L-arm. The groups of cables 37 and 38 are also visible in FIG. 5 where it may be seen that they run into the back of box 35. The cables extend from box 35 to box 40 through a flexible sheath or tube 41 which has a corrugated appearance. Tube 41, in this example, is comprised of a helically wound wire spring covered with an opaque plastic film. The tube provides an enclosure for the cables and keeps them collected loosely and, hence, without impairing such flexibility that they have. It will be evident from FIG. 5 that flexible cable enclosure tube 41 and the cable run therein are sufficiently long to permit the U-arm to be rotated about 100° in either direction about the horizontal axis of pintle 16.

A broken off section of flexible cable concealing tube similar to tube 41 is shown running out of box 40 in FIG. 5 and is marked 42. A continuation of this tube is similarly marked in FIGS. 1, 2 and 3. Flexible tube 42 runs up to the boom support in FIG. 2 which is generally designated by the reference numeral 45 and is part of the new cable handling device which will now be described in greater detail.

Figure 3:
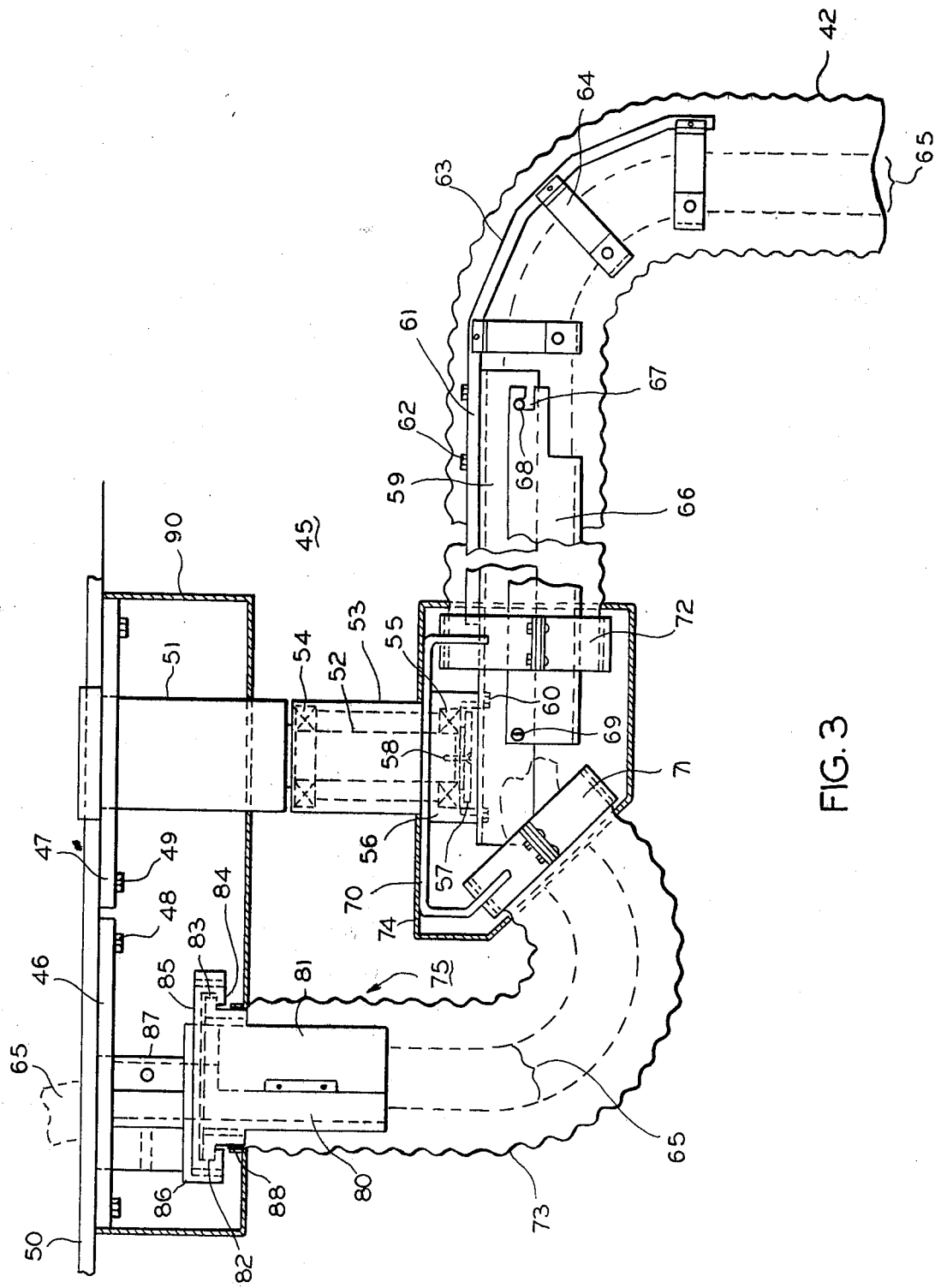
FIG. 3 shows the boom and swivel mechanism parts of the cable handling device, partially in section.
Figure 4:
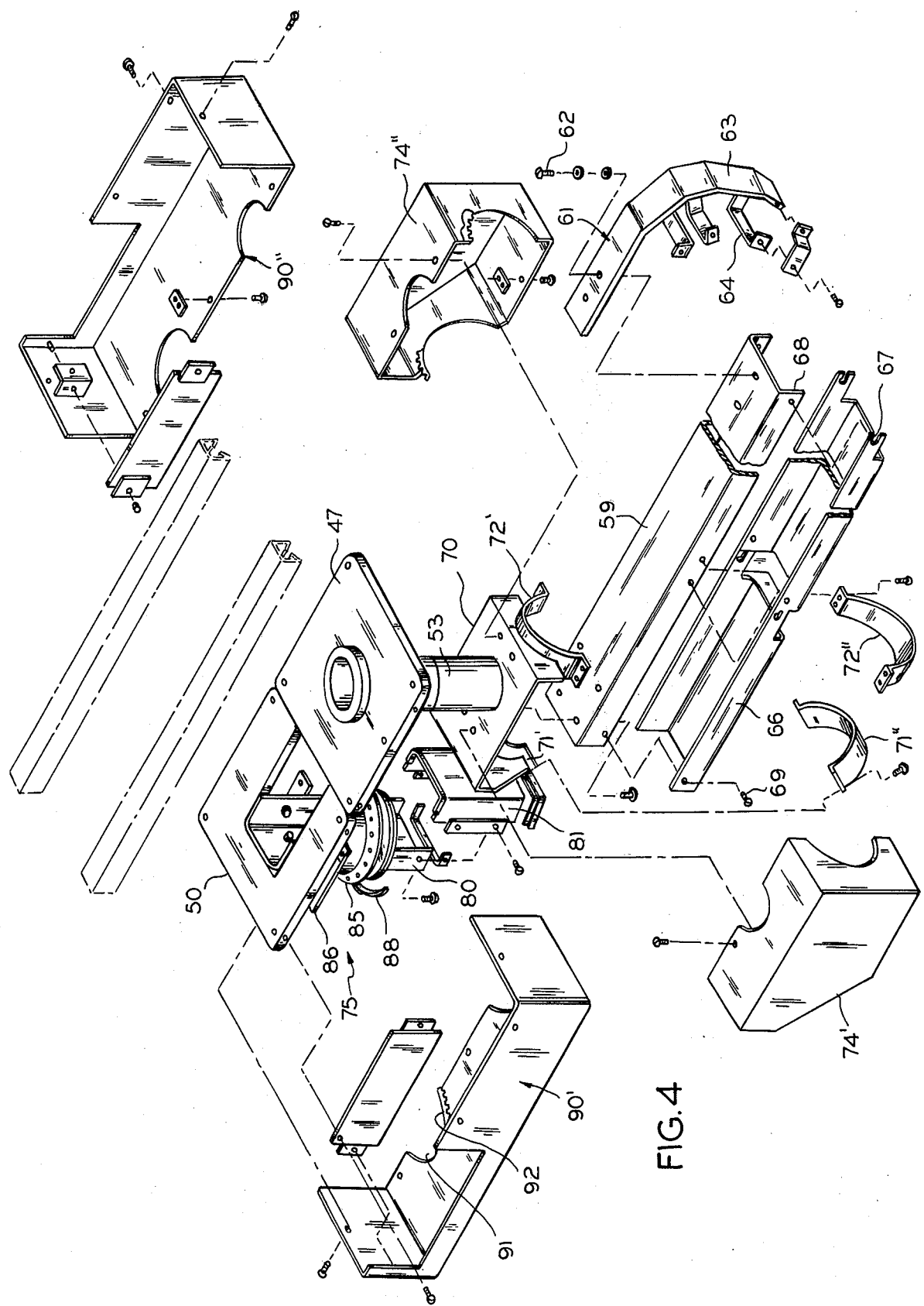
FIG. 4 is an exploded view of the cable handling boom together with its supporting axle and cooperating swivel mechanism; and, FIG. 5 shows a part of the x-ray equipment depicted in FIG. 2 as viewed from the front side of that figure.

The main parts of the boom assembly are shown in FIG. 3 and an exploded view, showing more details, is presented in FIG. 4.

Referring to FIG. 3, the boom assembly uses two plates 46 and 47 as the main supporting elements. The plates are fastened such as with bolts 48 and 49 to spaced apart pairs of stationary overhead beams, one of which is visible in FIG. 3 and is marked 50. These beams are usually concealed in the ceiling of the room in which the x-ray equipment is installed. The boom assembly includes a cylindrical axle support member, 51, mounted on fixed plate 47, and from which a stationary shaft or axle 52 projects. A sleeve 53 surrounds axle 52. The sleeve has internal shoulders for accepting upper and lower ball bearings 54 and 55. The lower end of the sleeve is diametrically enlarged such as at 56 and there is a recess within the enlargement for accommodating a clamping plate 57 which is fastened to the lower end of axle 52 with several machine screws such as the one marked 58. Clamping plate 57 retains sleeve 53 and bearings 54 and 55 on the axle and enables the enlarged portion 56 of the sleeve to support a load.

There is a horizontally extending channel member 59, constituting a part of the cable supporting horizontally swingable boom, fastened to the bottom face of enlarged portion 56 with several bolts, one of which is marked 60 in FIG. 3 and similarly in FIG. 4. A rigid cable supporting arm 61 is fastened to the closed top of channel member 59 by means of bolts such as the one marked 62. Arm 61 has a downwardly offset or curved portion 63 to which several cable surrounding split clamps 64 are fastened. The details of these clamps are evident in FIG. 4. The group of cables running up from box 40 on the x-ray equipment through flexible tube 42 are represented by spaced apart dashed lines marked 65 in FIG. 3. These cables all run through clamps 64 and through the length of channel 50 loosely and the cables are not tied in a bundle so they maintain any flexibility which they may have. Another channel member 66 is arranged in complementary fashion relative to channel 59 so that a duct is developed between them. Channel 66 is adapted for being swung downwardly away from channel 59 to facilitate threading the group of cables 65 through the duct without requiring the efforts of more than one serviceman. For this purpose, opposite sides of channel 66 are provided near their ends with hook-shaped notches 67 which engage with a pair of pins 68 that are fixed in the sides of channel 59 to provide a pivot. After the cables are fed through, channel 66 is swung into the position in which it is depicted in FIG. 3 and secured with screws such as the one marked 69 to form a duct which is closed on its top and bottom.

Also supported from axle sleeve 53 is a plate member 70. This member supports pairs of split clamping rings which are generally designated by the reference numerals 71 and 72. Clamping ring 72 is for fastening flexible cable concealing tube 42 at its upper end. Clamping ring 71 is for fastening one end of another short cable protecting and concealing flexible tube section 73 which runs to a swivel mechanism that is generally designated by the reference numeral 75 and will be described later. Parts of split clamping ring 71 are marked with the numerals 71' and 71" in FIG. 4. Parts of split clamping ring 72 in FIG. 3 are marked 72' and 72" in FIG. 4 where the bolts for forming the rings are shown and not marked but their place of insertion should be evident in the exploded view. The parts which are supported from the lower end of axle sleeve 53 are concealed within a sheet metal housing that is generally designated by the reference numeral 74 in FIG. 3 and is shown to be divided into two halves 74' and 74" in FIG. 4. The manner in which the housing halves are fastened to support member 70 in FIG. 4 is self-evident.

The vertical axis of axle 52 about which the boom, comprised of channels 59 and 66 and the curved arm extension 63 pivots, when extrapolated downwardly, should preferably intersect as near as possible with an extrapolation of the vertical axis of the L-arm floor bearing. The vertical axes should also preferably intersect with the horizontal rotational axis of the U-arm. This relationship keeps the outer end of the boom tracking the upright 11 on the L-arm 15 as closely as possible when the L-arm is swung concurrently with the boom arm. However, the boom and L-arm rotational axes may be misaligned substantially when necessary to avoid interferences without causing loss of tracking nor causing undue stress in the cables.

As previously mentioned, the cable group 65 continues from the axle supported housing 74 through a short section of flexible protective tube 73 to a swivel mechanism which is generally designated 75 and is shown in detail in FIGS. 3 and 4. The cable group 65 exits from the swivel mechanism and runs to various electrical devices in the building which are necessary for controlling operations of the x-ray equipment.

Swivel mechanism 75 comprises a split collar assembly comprised of two parts 80 and 81 which are joined with each other to form a vertical duct. Part 80 has a circular bearing flange 82 on it which is supported in a raceway 83 formed by axially spaced apart and apertured plates 84 and 85. Plate 85 mounts to a bracket plate 86 that is fastened to a split collar assembly 87 which provides a duct through which the entering and exiting cable group 65 extends. Flexible protective tube 73 is clamped with a band 88 to the collar assembly. The swivel mechanism, by virtue of its rotation, eliminates the torsional forces that would otherwise be built up on the twisted cable enclosure which could retard the free motion of the horizontally swinging cable supporting boom and the L and U arms also.

As can be seen in FIGS. 2, 3 and 4, the swivel mechanism and axle assembly are enclosed in a box 90 next to the ceiling. As shown in the FIG. 4 exploded view, box 90 is made up of two mating parts marked 90' and 90". The upstanding walls of the box parts are secured to the edges of the swivel mechanism and axle ceiling mounted plates 47 and 50 with screws as is evident in the drawing. The hole 91 through which flexible protective tube 73 and the enclosed cables enter the box is provided with a plastic edging 92, a fragment of which is shown, so the edges of the box will not wear through the tube. Other places where the flexible cable enclosing tubes such as 42 and 73 pass through holes are also provided with plastic edging as further illustrated on the box or cover part 74" in FIG. 4.

In a commercial design, a swivel connection is also made where the upper end of protective tube 41 enters box 35 on the U-arm as shown in FIG. 5. This minimizes the torsional forces which otherwise might be built up in this short protective tube and the cables therein when the U-arm is swung around the horizontal axis of pintle 16.

The cable handling device minimizes the restraint that would otherwise be imposed on the L and U arm equipment by the cables. When the L-arm 10 is swung in a circle, the boom simply follows it around with minimum restraint. The fact that the cables 65 are confined loosely in flexible protective tube 42 permits the cables to avoid mutual interaction with each other which, if it were not the case, would result in cable stiffness and greater forces being applied to the equipment when it is in certain angular positions.

Although a preferred embodiment of the new cable handling device has been described in detail, such description is intended to be illustrative rather than limiting, for the invention may be variously embodied and is to be limited only by interpretation of the claims which follow.

We claim:

1. A device for handling a group of cables which extend in a room to and from movable x-ray equipment which is located in the room, said cable handling device comprising:

axle means mounted above said equipment and a generally horizontally extending boom arm for supporting said cable group, said boom arm comprising two channel members one of which is fastened to said axle means and the other of which is fastened in complementary relation to said one channel member to define a duct for swinging about a vertical axis and for supporting a portion of said cable group passing through said duct generally horizontally with another continuous portion of said cable group extending beyond the support of said boom arm being directed generally downwardly to said x-ray equipment, clamping means surrounding said boom arm duct and supported from said axle means, and a flexible tubular enclosure through which said cable group runs, said tubular enclosure having an upper end portion surrounding said boom arm and engaged by said clamping means and being swingable with said boom arm and having a lower end portion coupled to said x-ray equipment, a swivel mechanism having a passageway for enabling said group of cables to run generally vertically and then to become generally horizontal on said boom arm, said swivel mechanism being rotatable about an axis spaced from the axis of said axle means, and a flexible tubular enclosure surrounding the cable portion between said swivel mechanism and said boom arm and having one end fastened to said boom arm and an opposite end fastened to said swivel mechanism to enable relieving the twist which would be otherwise imparted to said tubular enclosure by swinging of said boom arm.

2. A device for handling a group of cables which extend in a room to and from x-ray equipment, said equipment including: An L-arm comprised of unitary vertical and horizontal sections, the horizontal section being supported on one end for enabling said section to rotate about a vertical axis in a horizontal plane; a U-arm comprising a base section mounted on said vertical section of the L-arm for rotation in vertical planes about a horizontal axis and a pair of radially spaced apart arm sections projecting from said base section; and, x-ray imaging and x-ray source means mounted on said spaced apart arm sections, respectively, said cable handling device comprising:

axle means mounted above said equipment and generally horizontally extending boom arm means for supporting said cable group, said boom arm means comprising two channel members one of which is fastened to said axle means and the other of which is fastened to said one channel member to define a duct for swinging about a vertical axis and for supporting a portion of said cable group passing through said duct generally horizontally with another continuous portion of said cable group extending beyond the support of said boom means being directed generally downwardly to said x-ray equipment, clamping means surrounding said boom arm duct and supported from said axle means, and a flexible tubular enclosure surrounding said boom arm means and the portion of the group of cables running on said means and surrounding the portion of said group of cables extending between said boom arm means and said x-ray equipment, a swivel mechanism having a passageway for enabling said group of cables to run generally vertically and then to become generally horizontal on said boom arm means, said swivel mechanism being rotatable about a vertical axis in parallel spaced relationship with the axis of said axle means, and a flexible tubular enclosure surrounding the cable portion between said swivel means and said boom arm means and having one end fastened to said boom arm means and an opposite end fastened to said swivel means to enable relieving the twist which would otherwise imparted to said tubular enclosure by swinging of said boom arm means.

3. The device as in claim 2 including:

first box means mounted to said vertical section of said L-arm and second box means mounted to said base section of said U-arm, said cable group extending from said second box means to and through said first box means, the aforementioned tubular enclosure being coupled to said first box means to enable said enclosure to surround the cable group as aforesaid, and another flexible tubular enclosure extending between the first and second box means for surrounding said cable group extending between said boxes.

4. A device for handling a group of cables which extend in a room to and from x-ray equipment, said equipment including: An L-arm comprised of unitary vertical and horizontal sections, the horizontal section being supported on one end for enabling said section to rotate about a vertical axis in a horizontal plane; a U-arm comprising a base section mounted on said vertical section of the L-arm for rotation in vertical planes about a horizontal axis and a pair of radially spaced apart arm sections projecting from said base section; and, x-ray imaging and x-ray source means mounted on said spaced apart arm sections, respectively, said cable handling device comprising:

axle means mounted above said equipment and generally horizontally extending boom arm means for supporting said cable group, said boom arm means being mounted to said axle means for swinging about a vertical axis and for supporting a portion of said cable group generally horizontally with another continuous portion of said cable group extending beyond the support of said boom arm means being disposed downwardly for coupling to said x-ray equipment, a swivel mechanism having a passageway for enabling said group of cables to run generally vertically and then to become generally horizontal on said boom arm means, said swivel mechanism being rotatable about an axis that is spaced from the axis of said axle means, a first flexible tubular enclosure surrounding the cable portion between said swivel means and said boom arm means and having one end fastened to said boom arm means and an opposite end fastened to said swivel means to enable relieving the twist which would be otherwise imparted to said tubular enclosure by swinging of said boom arm means, and a second flexible tubular enclosure surrounding the portion of the group of cables extending between said boom arm means and said x-ray equipment.

5. The device as in claim 4 wherein said boom arm means comprises a first channel-shaped member having its top closed side fastened at an end thereof to said axle means and its open side facing downwardly, a second channel-shaped member arranged in complementary relation to said first member to define a duct between them for said cable group to run through.

6. The device as in claim 5 wherein said first channel-shaped member has pins projecting from it near one of its ends and said second channel member has hook-shaped slots near its corresponding end for engaging said pins to enable said second member to be engaged with said pins and swung into said complementary relation with said first member and form said duct after said cable group has been run along said boom arm, and means for securing said second member against pivoting relative to said first member to thereby maintain said duct.

* * * * *